US010960161B2

(12) United States Patent
Armitstead et al.

(10) Patent No.: US 10,960,161 B2
(45) Date of Patent: Mar. 30, 2021

(54) METHOD AND APPARATUS FOR IMPROVED FLOW LIMITATION DETECTION OF OBSTRUCTIVE SLEEP APNEA

(71) Applicant: ResMed Pty Ltd, Bella Vista (AU)

(72) Inventors: Jeffrey Peter Armitstead, Sydney (AU); Chinmayee Somaiya, Sydney (AU)

(73) Assignee: ResMed Pty Ltd

( * ) Notice: Subject to any disclaimer, the term of this patent is extended or adjusted under 35 U.S.C. 154(b) by 511 days.

(21) Appl. No.: 15/923,480

(22) Filed: Mar. 16, 2018

(65) Prior Publication Data

US 2018/0272088 A1    Sep. 27, 2018

Related U.S. Application Data

(63) Continuation of application No. 14/082,429, filed on Nov. 18, 2013, now Pat. No. 10,004,862, which is a
(Continued)

(51) Int. Cl.
*A61M 16/00* (2006.01)
*A61B 5/087* (2006.01)
*A61B 5/00* (2006.01)

(52) U.S. Cl.
CPC ...... *A61M 16/024* (2017.08); *A61M 16/0069* (2014.02); *A61M 16/021* (2017.08);
(Continued)

(58) Field of Classification Search
CPC ............. A61M 16/00; A61M 16/0003; A61M 16/0051; A61M 16/021; A61M 16/022;
(Continued)

(56) References Cited

U.S. PATENT DOCUMENTS

| 5,148,802 A | 9/1992 | Sanders et al. |
| 5,245,995 A | 9/1993 | Sullivan et al. |

(Continued)

FOREIGN PATENT DOCUMENTS

| EP | 0927538 A2 | 7/1999 |
| JP | H07504347 A | 5/1995 |

(Continued)

OTHER PUBLICATIONS

Alan R Schwartz. Philip L Smith, Isaac Bankman and Solbert PERMUn, "Effect of Positive Nasal Pressure on Upper Airwa pressure-Flow Relationships", Journal of Applied Physiology, 1989,66: pp. 1626-1634.
(Continued)

*Primary Examiner* — Colin W Stuart
(74) *Attorney, Agent, or Firm* — Botos Churchill IP Law LLP

(57) ABSTRACT

In a respiratory apparatus for treatment of sleep apnea and other disorders associated with an obstruction of a patient's airway and which uses an airflow signal, an obstruction index is generated which detects the flattening of the inspiratory portion of the airflow. The flattening index serves as an obstruction index used to differentiate normal and obstructed breathing. The obstruction index is based upon comparison of values of airflow in different sectors of the inspiratory peak of the wave function and is particularly suitable for distinguishing M shaped or square shaped respiratory patterns indicative of partially obstructed airways.

22 Claims, 8 Drawing Sheets

Related U.S. Application Data continuation of application No. 12/097,102, filed as application No. PCT/AU2007/000272 on Mar. 6, 2007, now Pat. No. 8,607,793.

(60) Provisional application No. 60/779,577, filed on Mar. 6, 2006.

(52) U.S. Cl.
CPC ........ *A61M 16/022* (2017.08); *A61M 16/026* (2017.08); *A61B 5/087* (2013.01); *A61B 5/4818* (2013.01); *A61M 2016/003* (2013.01); *A61M 2016/0015* (2013.01); *A61M 2016/0018* (2013.01); *A61M 2016/0021* (2013.01); *A61M 2016/0027* (2013.01); *A61M 2016/0033* (2013.01); *A61M 2016/0036* (2013.01); *A61M 2205/33* (2013.01); *A61M 2205/3327* (2013.01); *A61M 2205/3331* (2013.01); *A61M 2205/3334* (2013.01); *A61M 2205/3344* (2013.01); *A61M 2206/10* (2013.01); *A61M 2230/005* (2013.01); *A61M 2230/40* (2013.01)

(58) Field of Classification Search
CPC .............. A61M 16/024; A61M 16/026; A61M 2016/0015; A61M 2016/0018; A61M 2016/0027; A61M 2016/003; A61M 2016/0033; A61M 2016/0021; A61M 2016/0036; A61M 2205/33; A61M 2205/3331; A61M 2205/3334; A61M 2210/1025; A61M 2210/1028; A61M 2210/1032; A61M 2210/1035; A61M 2210/1039; A61B 5/087; A61B 5/091; A61B 5/08; A61B 5/4818

See application file for complete search history.

(56) References Cited

U.S. PATENT DOCUMENTS

| | | | |
|---|---|---|---|
| 5,335,654 A | 8/1994 | Rapoport | |
| 5,632,269 A | 5/1997 | Zdrojkowski | |
| 5,645,053 A | 7/1997 | Remmers et al. | |
| 5,675,797 A | 10/1997 | Chung et al. | |
| 5,704,345 A | 1/1998 | Berthon-Jones | |
| 5,803,066 A * | 9/1998 | Rapoport ............. | A61B 5/0002 128/204.21 |
| 6,626,175 B2 * | 9/2003 | Jafari .................. | A61M 16/205 128/204.21 |
| 6,814,073 B2 | 11/2004 | Wickham | |
| 7,013,893 B2 | 3/2006 | Wickham et al. | |
| 7,827,988 B2 | 11/2010 | Matthews et al. | |
| 7,938,114 B2 | 5/2011 | Matthews et al. | |
| 2002/0043264 A1 * | 4/2002 | Wickham .......... | A61M 16/0069 128/204.18 |
| 2005/0241639 A1 | 11/2005 | Zilberg | |
| 2006/0000475 A1 | 1/2006 | Matthews et al. | |
| 2007/0142741 A1 * | 6/2007 | Berthon-Jones .... | A61M 16/024 600/534 |

FOREIGN PATENT DOCUMENTS

| | | |
|---|---|---|
| JP | 2000-217802 A | 8/2000 |
| JP | 2004506499 A | 3/2004 |
| JP | 2004533270 A | 11/2004 |
| JP | 2005505347 A | 2/2005 |
| JP | 2005505437 A | 2/2005 |
| JP | 2005103311 A | 4/2005 |
| JP | 2007512049 A | 5/2007 |
| WO | 93/09834 A1 | 5/1993 |
| WO | 0218002 A1 | 3/2002 |
| WO | 03030804 A2 | 4/2003 |
| WO | 2004012597 A1 | 2/2004 |
| WO | 2005077447 A1 | 8/2005 |
| WO | 2005107590 A1 | 11/2005 |
| WO | 2006066337 A1 | 6/2006 |

OTHER PUBLICATIONS

Extended European Search Report for Application No. EP07718545 dated Jan. 22, 2013.
Japanese Office Action for Application No. P2012-107924 dated Jul. 2, 2013.
Office Action from Japanese Application No. 2008-557549 dated Dec. 19, 2011.
Philip L Smith, Robert A Wise, Avram R Gold, Alan R Schwartz, and Solbert PERMun (with technical assistance of Norman Schubert), "Upper Airway Pressure-Flow Relationships in Obstructive Sleep Apnea", Journal of Applied Physiology, 1988, 64(2): pp. 789-795.

* cited by examiner

METHOD AND APPARATUS FOR IMPROVED FLOW LIMITATION DETECTION OF OBSTRUCTIVE SLEEP APNEA

CROSS-REFERENCE TO RELATED APPLICATIONS

The present application is a continuation of U.S. patent application Ser. No. 12/097,102, filed Oct. 10, 2008, which is a national phase entry under 35 U.S.C. § 371 of International Application No. PCT/AU2007/000272 filed Mar. 6, 2007, published in English, which claims priority from U.S. Provisional Patent application No. 60/779,577 filed Mar. 6, 2006, all of which are hereby incorporated herein by reference.

FIELD OF THE INVENTION

This invention relates to an improved method and apparatus for the diagnosis and treatment of respiratory conditions including sleep apnea or hypopnea. In particular it relates to detecting either partial or complete obstruction of the airway of a patient, based upon an analysis of the time development of an inspiratory portion of a respiratory airflow curve. It also relates to apparatus that adjust treatment pressure to be applied by a CPAP ventilator.

BACKGROUND OF THE INVENTION

Obstructive Sleep Apnea (OSA), a syndrome that includes apnea, hypopnea and heavy snoring, causes sleep disruption that brings about serious health problems possibly including types of heart disease. OSA is caused by the collapse of portions of a person's airway passage. The treatment of choice for OSA is the administration of Continuous Positive Airway Pressure (CPAP) to keep the patient's airway open. The air, usually in the pressure range 4-20 cm $H_2O$, is supplied by a motor driven blower whose output passes via an air delivery device to sealingly engage a patient's airway. A mask, tracheotomy tube, endotracheal tube, nasal pillows or other appropriate device may be used. An exhaust port is provided in a delivery tube proximate to the air delivery device. Some CPAP devices, termed bi-level CPAP, sense the breathing cycle of inspiration and expiration and provide different positive pressure levels during inhaling and exhaling. Some self-titrating CPAP devices are designed to determine appropriate pressure levels for the individual patient by selecting the least pressure that resolves the OSA. In such devices patterns of respiratory parameters are monitored to determine when OSA is present, and CPAP pressure is raised on the detection of appropriate patterns to provide increased airway pressure to, ideally, subvert the occurrence of obstructive episodes and the other forms of breathing disorder. Such devices are described in U.S. Pat. Nos. 5,148,802 and 5,245,995.

Typically a person suffering from OSA is diagnosed and treated in a sleep laboratory where the presence of the ailment is confirmed during a first night sleeping session and the appropriate treatment pressure is determined during a second night sleeping session. One problem that arises is that the appropriate pressure varies during the night as the person goes through different stages of sleep. Therefore there has been a long felt need for simplified apparatus for use in a patient's own home that could determine the presence of OSA and modify the pressure level to an optimum pressure. There have been several attempts, with varying success, to determine the presence of OSA from the analysis of the shape of airflow curves as a function of time.

The monitoring of upper airway pressure-flow relationships in obstructive sleep apnea has been described in Smith et al., 1988, J. Appl Physiol. 64: 789-795. FIG. 1 of that article shows polygraphic sleep recordings at varying levels of increasing nasal pressure. It was noted that inspiratory volumetric flow plateaued in certain breaths suggesting the presence of airflow limitation. Pressure-flow curves were constructed by plotting mid-inspiratory airflow against either mask pressure or endoesophageal pressure. The pressure-flow plots of nasal pressure against mean midinspiratory flow were then fit by least-squares linear regression to calculate resistance upstream to the collapsible-site.

The effect of positive nasal pressure on upper airway pressure-flow relationships has been described in Schwartz et al., 1989, J. Appl Physiol. 66: 1626-1634. FIG. 4 of the article shows that pressure-flow tracings plateau at a low pressure level. It was further shown when the pressure was increased, flow did not plateau.

U.S. Pat. No. 5,335,654 (Rapoport) shows the effect of CPAP on the airflow versus time curve for a patient suffering from OSA. FIGS. 1-5 in Rapoport show that as the pressure is reduced from 10 cm $H_2O$ to 2 cm $H_2O$ in steps of 2 cm $H_2O$ the curve of airflow versus time changes from an almost smooth sinusoidal pattern to one with a flattening of the inspiration portion of the curve with initial and terminal flow spikes. At 2 cm $H_2O$ the curve has developed a so-called M shape (i.e. with a ripple in the middle) and has also developed overshoots (i.e. peaks) at each end of the flattened central region. In an attempt to characterize the flow shapes that indicate obstruction, Rapoport lists several indices said to be indications of flow limitation and/or partial obstruction patterns including: (1) The derivative of the flow signal equals zero; (2) The second derivative between peaks of the flow signal is zero for a prolonged interval; (3) The ratio of early inspirational flow to mid-inspirational flow is less than or equal to 1. The patent further lists events said to be indications of obstructions: (1) Reduced slope of the line connecting the peak inspiratory flow to the peak expiratory flow; (2) Steep upward or downward stroke (dV/dt) of the flow signal; and (3) Ratio of inspiratory flow to expiratory flow over 0.5.

With regard to the control of CPAP treatment, various techniques are known for sensing and detecting abnormal breathing patterns indicative of obstruction. For example, U.S. Pat. No. 5,245,995 (Sullivan et al.) describes how snoring and abnormal breathing patterns can be detected by inspiration and expiration pressure measurements while sleeping, thereby leading to early indication of pre-obstructive episodes or other forms of breathing disorder. Particularly, patterns of respiratory parameters are monitored, and CPAP pressure is raised on the detection of pre-defined patterns to provide increased airway pressure to ideally prevent the occurrence of the obstructive episodes and the other forms of breathing disorder.

U.S. Pat. No. 5,645,053 (Remmers) describes calculating a flatness index, wherein flatness is defined to be the relative deviation of the observed airflow from the mean airflow. In Remmers, individual values of airflow are obtained between 40% and 80% of the inspiratory period. The mean value is calculated and subtracted from individual values of inspiratory flow. The individual differences are squared and divided by the total number of observations minus one. The square root of this result is used to determine a relative variation.

The relative variation is divided by the mean inspiratory airflow to give a relative deviation or a coefficient of variation for that breath.

U.S. Pat. No. 5,704,345 (Berthon-Jones) disclosed a method for detecting partial obstruction of a patient's airway by calculating two obstruction index values that parameterize a flattening of an inspiratory portion of a patient's monitored respiratory airflow. Either obstruction index is then compared to a threshold value. The first shape factor involves a ratio of the mean of a mid-portion of the inspiratory airflow of the breathing cycle and the mean of the inspiratory airflow.

$$shape1 = \frac{\frac{1}{33}\sum_{t=16}^{48} fs(t)}{M}$$

where fs(t) is a sample of the patient inspiratory airflow and M is the mean of inspiratory airflow given by $$M = \frac{1}{65}\sum_{t=1}^{65} fs(t).$$

The second shape factor involves a ratio of the Root Mean Square deviation of a mid-portion of inspiratory airflow and the mean inspiratory airflow according to the formula $$shape2 = \frac{\sqrt{\frac{1}{33}\sum_{t=16}^{48} (fs(t) - M)^2}}{M}.$$

U.S. Pat. No. 6,814,073 (Wickham) discloses a method and apparatus for detecting some forms of obstruction based upon the inspiratory airflow. In this method, inspiratory airflow samples corresponding to mid-inspiration are identified. In one embodiment, weighting factors are applied based on whether the inspiratory airflow samples are less than or greater than a threshold level, such as the mean airflow. In another embodiment, different weighting factors are applied to samples based on their time positions in a breath. Samples taken prior to a certain event during inspiration, for example samples preceding the half way point of inspiration, are assigned lower weighting factors than samples succeeding the event. An obstruction index is then calculated using these samples with their corresponding weighting factors.

All these disclosed techniques fail to detect flow limitation in certain types of flow patterns, particularly the M-wave pattern. More generally, flow limitation in the inspiratory patterns that present with leading or lagging overshoot, is not appropriately detected. The detectability depends on two factors. 1) the extent to which the overshoot-traverses the mid-portion of the inspiratory airflow, and 2). the size of the overshoot. The solution presented by Wickham, works satisfactorily if the size of the overshoot is relatively small, does not span a large portion of mid-inspiration, and is not present in the latter half of the inspiratory airflow.

However, flattening indices from the Wickham method are sometimes not as accurate as the indices from the method disclosed by Berthon-Jones. One aspect of the present invention is to simplify the algorithm mentioned in U.S. Pat. No. 5,704,345 (Berthon-Jones), the disclosure of which is incorporated by reference. Thus, an objective of the current invention is to present a method by which flow-limitation can be detected in the presence of the mentioned limitations, particularly the M wave pattern with overshoots.

The flow limitation detection/estimation technique described by the prior art is also expensive in terms of digital processing power, and the accuracy of flow detection required. Therefore its utility in low cost electronic/software platforms is limited. Therefore another objective of the present invention is to simplify the algorithm to render it more amenable to low-end electronic and software platforms.

BRIEF SUMMARY OF THE INVENTION

The present invention involves an improved method and apparatus for detecting some forms of respiration obstruction based upon the flattening of the inspiratory airflow.

One aspect of the invention is a method for detecting partial obstruction of the airway of a patient, the method comprising the steps of Measuring respiratory air flow from the patient; Detecting the inspiratory part of that airflow; Trimming the inspiratory part to remove any expiratory pause; Normalizing the effect of offshoot; Scaling the inspiratory flow to a reference value; Calculating the mean deviation of a central portion of the inspiratory air flow; Calculating a flattening index from the mean deviation; and Filtering the flattening index with a moving average filter.

In connection with the method for detecting partial obstructions, a normalizing correction is made for overshoots that would otherwise exaggerate the roundness estimate of the inspiratory airflow.

In an embodiment of the invention the normalization of the overshoot is accomplished by truncating airflow values outside a central portion of the inspiratory airflow that exceed the average value of a central portion of the inspiratory airflow.

In another embodiment of the invention, the overshoot is evaluated by dividing the inspiratory airflow wave into multiple parts, calculating mean amplitudes for each part, analyzing the mean amplitudes to determine the presence of overshoot, and, if overshot is indicated, treating flattening as low.

In a further embodiment of the invention, a hunt for maximal flatness is carried out by calculating a set of flattening indices for each possible sample in a middle part of the inspiratory wave form and taking the flattening index for the inspiratory waveform to be the minimum of the calculated indices.

Hence it is an aspect of the invention to estimate the extent of flow limitation in patient breath by the extent to which the position of peak flow deviates from the center of the inspiration flow curve.

It is a further aspect of the invention to estimate the flow limitation by the extent to which the relative mean amplitude of different parts of the breath deviate from the pattern exhibited by normal breaths.

It is a still further aspect of the invention to provide a method to estimate the extent of flow limitation by hunting for the part of the breath that exhibits maximal flatness.

It is an objective of the present invention to provide an apparatus in which obstruction, either partial or complete, of the patient's airway is detected by analyzing respiratory airflow by a method for detecting partial obstruction of the airway of a patient, the method comprising the steps of Measuring respiratory air flow from the patient; Detecting the inspiratory part of that airflow; Trimming the inspiratory part to remove any expiratory pause; Normalizing the effect of offshoot; Scaling the inspiratory flow to a reference value; Calculating the mean deviation of a central portion of the inspiratory air flow; Calculating a flattening index from the mean deviation; and Filtering the flattening index with a moving average filter.

A further objective is to provide an apparatus in which an improved algorithm for detecting airway obstruction is implemented without using additional components or making substantial changes to the structure of existing respiratory apparatus.

Accordingly, a respiratory apparatus is provided in which the respiratory airflow of a patient is continuously monitored and the part of respiratory airflow associated with inspiration is identified and sampled.

In one aspect, the subject invention pertains to a respiratory apparatus which includes an air source adapted to selectively provide pressurized breathable air to a patient, a flow detecting device to sense the respiratory airflow from the patient and to generate an airflow signal indicative of airflow, an obstruction detector coupled to said flow sensor which implements a method for detecting partial obstruction of the airway of a patient, the method comprising the steps of Measuring respiratory air flow from the patient; Detecting the inspiratory part of that airflow; Trimming the inspiratory part to remove any expiratory pause; Normalizing the effect of offshoot; Scaling the inspiratory flow to a reference value; Calculating the mean deviation of a central portion of the inspiratory air flow; Calculating a flattening index from the mean deviation; and Filtering the flattening index with a moving average filter, and a pressure controller connected to a pressure sensor equivalent—either physically or logically arranged to control the operation of the air source, receive the obstruction signal and alter the operation of the air source in response to the obstruction signal. The term flow detecting device is intended to be a general term that includes flow sensors or alternative flow detecting devices or algorithms, such as, for example, those determining flow from a motor current.

Another aspect of the invention concerns an apparatus for monitoring and/or treating a patient having a sleep disorder, the apparatus including a flow detecting device that senses patient respiration and generates a corresponding flow signal; and an obstruction detector coupled to the flow detecting device and adapted to implement a method for detecting partial obstruction of the airway of a patient, the method comprising the steps of Measuring respiratory air flow from the patient; Detecting the inspiratory part of that airflow; Trimming the inspiratory part to remove any expiratory pause; Normalizing the effect of offshoot; Scaling the inspiratory flow to a reference value; Calculating the mean deviation of a central portion of the inspiratory air flow; Calculating a flattening index from the mean deviation; and Filtering the flattening index with a moving average filter, wherein the obstruction detector including a signal generator that generates a signal indicative of an airway obstruction based on the flattening index.

A further-aspect of the invention concerns an apparatus for treating a patient having a sleep disorder, the apparatus comprising a mask, a gas source selectively supplying pressurized breathable air to the patient through the mask, a flow detecting device that senses airflow and generates a flow signal indicative of respiration, an obstruction detector coupled to the flow detecting device and adapted to implement a method for detecting partial obstruction of the airway of a patient, the method comprising the steps of Measuring respiratory air flow from the patient; Detecting the inspiratory part of that airflow; Trimming the inspiratory part to remove any expiratory pause, Normalizing the effect of offshoot, Scaling the inspiratory flow to a reference value, Calculating the mean deviation of a central portion of the inspiratory air flow, Calculating a flattening index from the mean deviation, and Filtering the flattening index with a moving average filter, and a controller receiving the obstruction signal and generating in response a command for activating the gas source.

Another aspect of the invention concerns a method for detecting obstruction in the airways of a patient, including measuring an air flow of the patient; detecting a predetermined section of said air flow, implementing a method for detecting partial obstruction of the airway of a patient, the method comprising the steps of Measuring respiratory air flow from the patient; Detecting the inspiratory part of that airflow; Trimming the inspiratory part to remove any expiratory pause; Normalizing the effect of offshoot; Scaling the inspiratory flow to a reference value; Calculating the mean deviation of a central portion of the inspiratory air flow; Calculating a flattening index from the mean deviation; and Filtering the flattening index with a moving average filter.

DETAILED DESCRIPTION

Apparatus and Methodology

Figure 1:
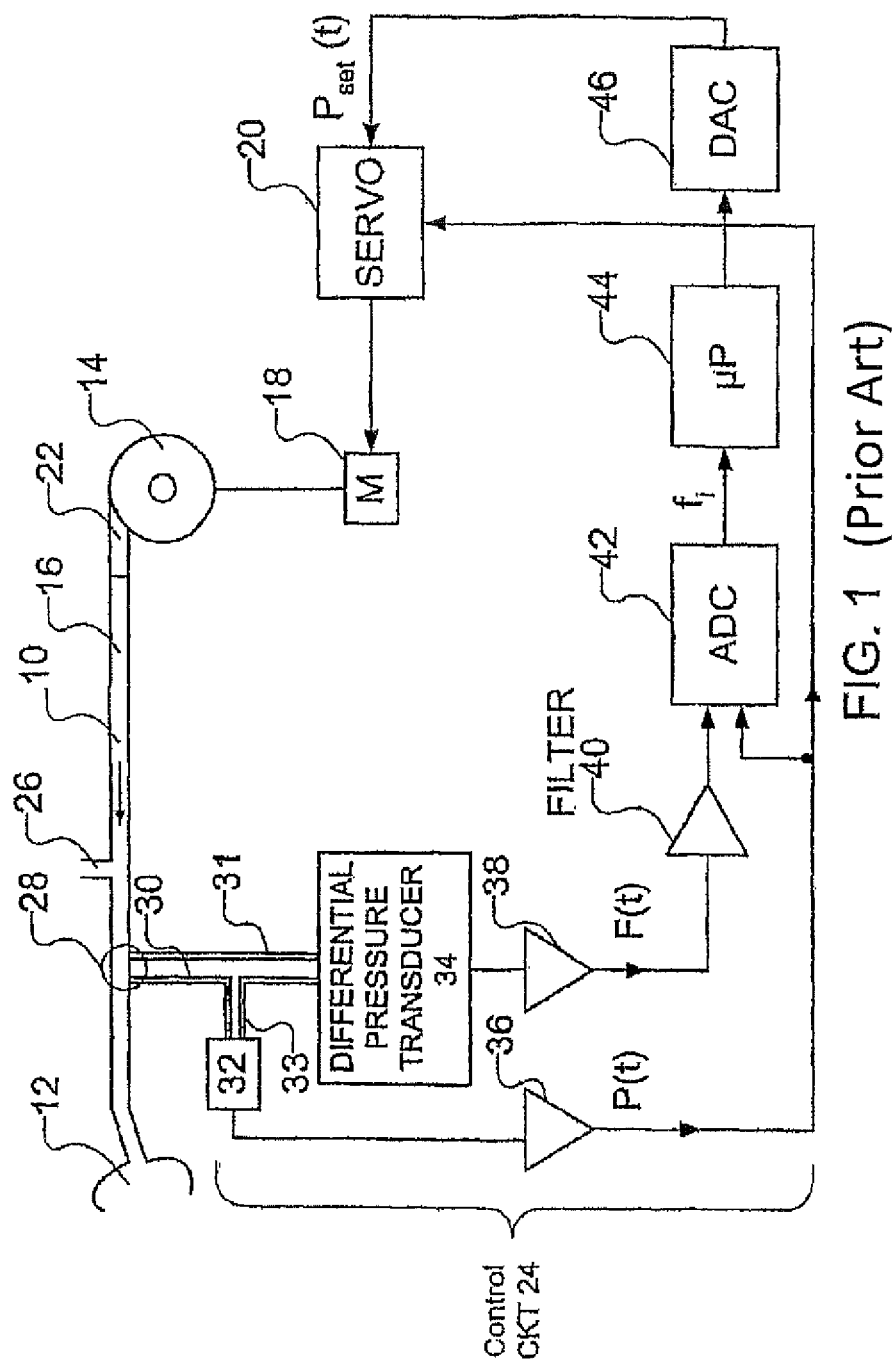
FIG. 1 shows a block diagram of a respiratory apparatus constructed in accordance with this invention.

FIG. 1 shows an example respiratory apparatus 10 constructed in accordance with the invention. The respiratory apparatus 10 includes a mask 12 connected to a blower 14 by a flexible tube 16. The mask 12 is fitted to the patient and may be either a nose mask or a facemask. The blower 14 has an air outlet 22 is driven by a motor 18 in accordance with control signals from a servocontroller 20. This arrangement allows the respiratory apparatus 10 to deliver pressurized air (or air enriched with oxygen from a source, not shown). The pressurized air is delivered by tube 16 to the mask 12. The tube 16 is provided with a narrow exhaust port 26 through which air exhaled by the patient is expelled.

A control circuit 24 is used to control the operation of servocontroller 20 and motor 18 using certain predetermined criteria, thereby defining modes of operation for the apparatus 10. Preferably, in accordance with this invention, the control circuit 24 is adapted to operate the apparatus 10 to provide CPAP to the patient.

Control circuit 24 includes a flow restrictive element 28. Tubes 30 and 31 lead from different sides of the restrictive element 28 to a mask pressure transducer 32 and a differential pressure transducer 34 respectively. The mask pressure transducer 32 is also connected through another tube 33 to the differential pressure transducer 34.

The mask pressure transducer 32 generates a first electrical signal, which is amplified by an amplifier 36 to generate an output P(t) proportional to the air pressure within the mask 12. This output is fed directly to the servocontroller 20.

The differential pressure transducer 34 senses the differential pressure across the flow restrictive element 28, which differential pressure is related to the airflow rate through the flow restrictive element 28 and tube 16.

Differential pressure transducer 34 generates a second electrical signal that is amplified by an amplifier 38. This amplified signal F(t) is termed an airflow signal since it represents the airflow through the tube 16. Alternatively, the flow may be derived from the motor current.

The airflow signal F(t) is fed to a filter 40 that filters the signal within a preset range. The outputs of the filter 40 and amplifier 36 are fed to an ADC (analog-to-digital) converter 42, which generates corresponding signals to a microprocessor 44. The microprocessor 44 generates analog control signals that are converted into corresponding digital control signals by DAC 46 and used as a reference signal Pset (t) for the servo 20.

Figure 2:
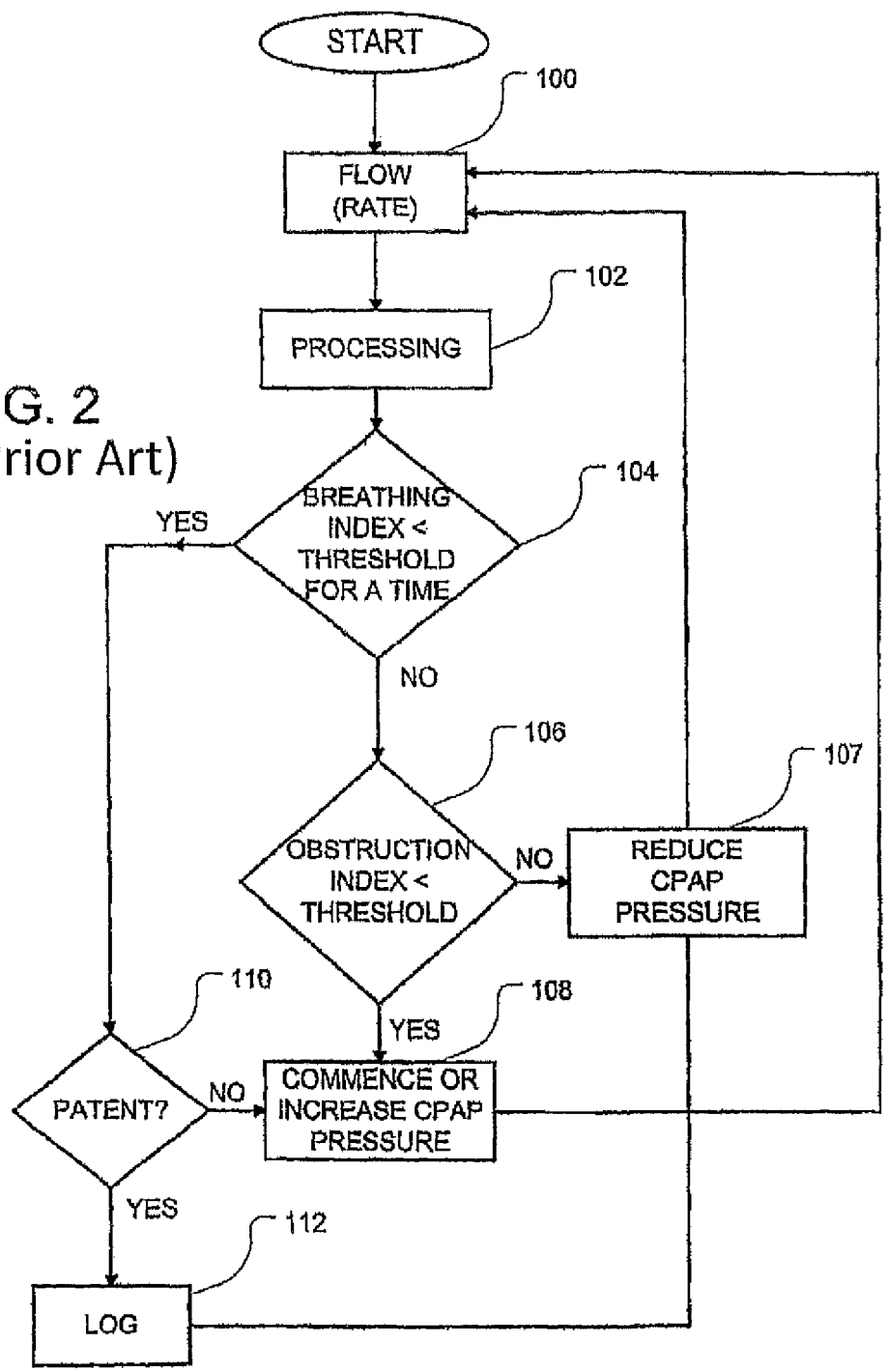
FIG. 2 shows a flow chart illustrating the operation of the apparatus of FIG. 1.

One method for the operation of a respiratory apparatus 10 is shown in the flow chart of FIG. 2. Individuals skilled in the art will recognize other methodologies for utilizing the improved flow flattening index that is disclosed herein. The embodiment of the methodology of FIG. 2 is also detailed in U.S. Pat. No. 5,704,345 (the '345 patent). The first step 100 is the measurement of respiratory flow over time. This information is processed in step 102 to generate Index values to be used as qualitative measures for subsequent processing. Thus, Step 102 includes the generation of obstruction index values based upon the averaging method as disclosed herein. Step 104 detects whether an apnea is occurring by comparison of the breathing Index with a threshold value.

If the answer in step 104 is "Yes", an apnea is in progress and there then follows a determination of patency in step 110 by methods disclosed in the mentioned Wickham or Berthon-Jones patents. If there is patency of the airway, a central apnea with an open airway is occurring, and, if desired, the event is logged in step 112. If the result of step 110 is that the airway is not patent, then a total obstructive apnea or a central apnea with closed airway is occurring, which results in the commencement or increase in CPAP treatment pressure in step 108. If desired, step 108 may include the optional logging of the detected abnormality. Alternatively, flattening is simply rejected when apnea occurs since the breath pattern will not satisfy the criteria of either the number of samples or the required tidal volume—that is required for a valid breath for flattening—when apnea is present.

If the answer in step 104 is "No", one or more obstruction indices, such as the improved flow flattening indices, are compared with threshold values in step 106, by which the determination of obstruction of the airway is obtained. If the answer is "Yes" in step 106, then there is a partial obstruction, and if "No", there is no obstruction (normalcy).

In the case of a complete or partial obstruction of the airway Step 108 applies and a consequential increase in CPAP treatment pressure occurs. In the instance of normal breathing with no obstruction, the CPAP treatment pressure is reduced, in accordance with usual methodologies that seek to set the minimal pressure required to obviate, or at least reduce, the occurrence of apneas. The amount of reduction in step 107 may, if desired, be zero. Similarly, in the event of a central apnea with patent airway (step 110, 112) treatment pressure is not increased. Such increases in pressure reflexively inhibit breathing, further aggravating the breathing disorder.

Improved Flow Flattening Indices

Figure 3:
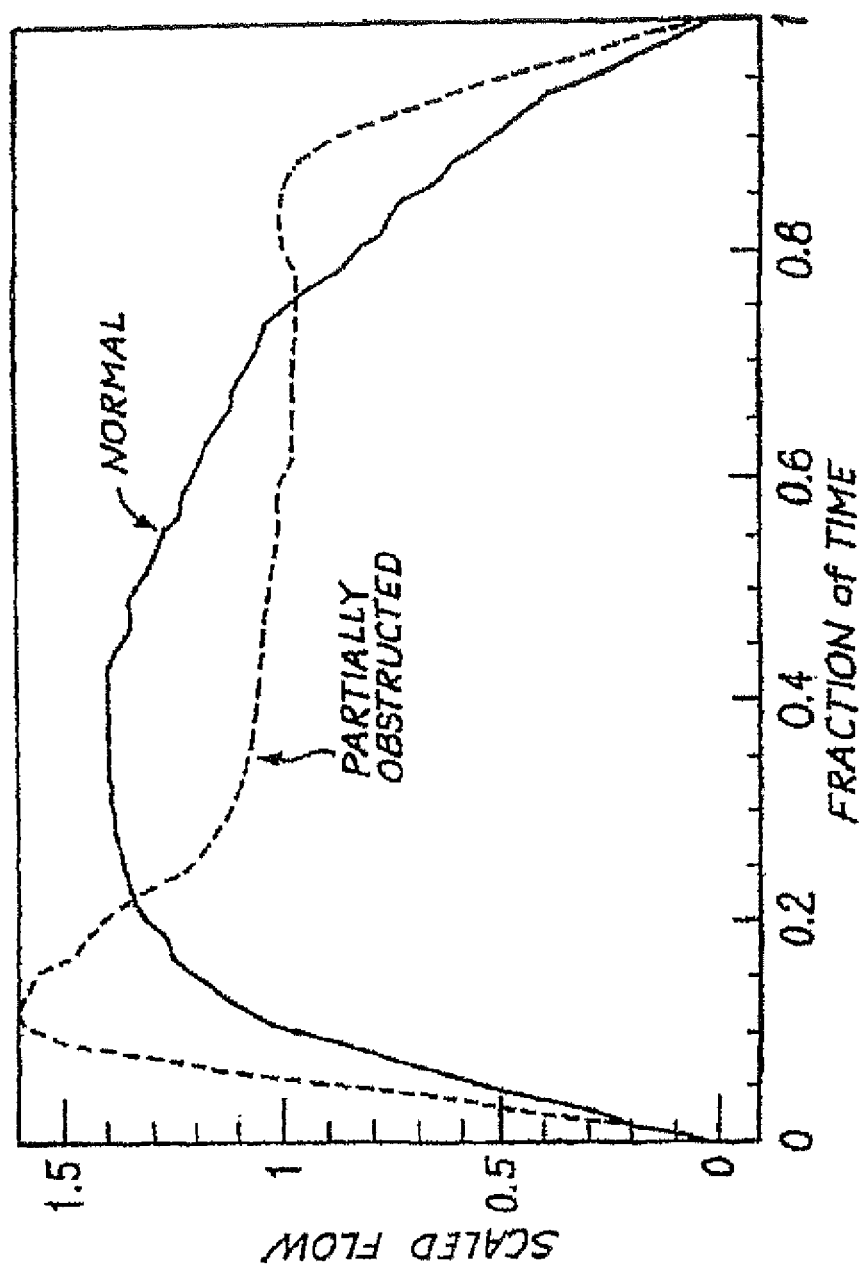
FIG. 3 shows the inspiration phases of typical respiration signals for a healthy person and a person with a partial airway obstruction.

FIG. 3 depicts an airflow signal with respect to the inspiratory portion of a typical breathing cycle. During the inspiratory portion of the breathing cycle of a healthy person (solid line), the airflow rises smoothly with inspiration, reaches a peak and falls smoothly to zero. However, a patient with a partially obstructed airway (dashed line) exhibits a breathing pattern characterized by a significant flat zone during inspiration. Theoretically, for an obstructed flow, as the degree of partial obstruction increases, the airflow signal for inspiration would tend to a square wave.

Detection of Inspiratory and Expiratory Half Cycles in Breathing

Figure 4:
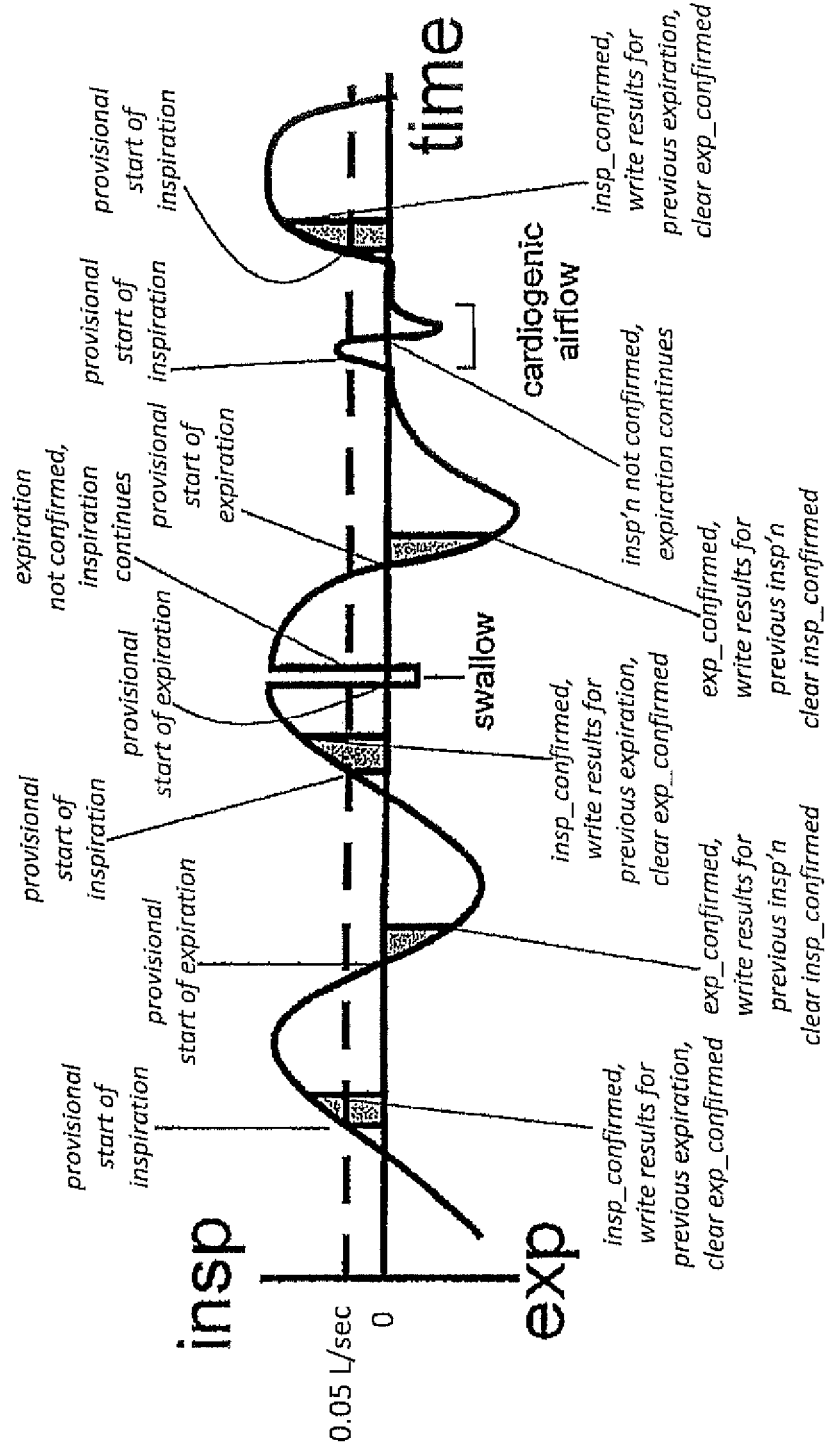
FIG. 4 shows a normal respiratory cycle.

As shown in FIG. 4, a normal respiratory cycle consists of inspiration and expiration and a brief end-expiratory pause. During the end-expiratory pause small oscillations in airflow due to heartbeat occur. In order to correctly detect the start of inspiration, it is necessary to ignore the small pulses of air due to heartbeat. Similarly it is necessary to ignore brief cessation due to swallowing.

The start of inspiration may be taken provisionally as the time that inspiratory airflow exceeds a threshold of about 0.05 L/sec. If the flow then falls below zero again before the total volume reaches about 0.1 liters, it is assumed that expiration is continuing.

The start of expiration is taken provisionally as the time that expiratory airflow falls below zero. If the airflow then goes above about 0.05 L/sec in the inspiratory direction before the total volume expired reaches about 0.1 liters, it is assumed that inspiration is continuing.

The purpose of the above algorithm is to detect the start and end of each respiratory half-cycle. This information is required for the shape detector. It is immune to events such as swallows and cardiogenic airflow (which do not achieve the 0.1 litre volume requirement). A normal breath has a peak flow of about 0.3 L/sec, and a tidal volume of 0.5 liters. Hence there is a 3 to 5-fold reserve ability to detect normal breaths. Since the timing information is used for shape algorithms, where very small breaths are irrelevant, it is not necessary to respond to extremely small breaths. Because the threshold crossing point is detected without further low pass filtering, the algorithm does not introduce phase delay.

Calculation of Curvature or Flattening Index

A normal inspiratory flow-time curve is rounded, or quasi-sinusoidal in shape. Diaphragm muscular effort available for producing airflow is low at the beginning and end of the breath, and high in the middle of the breath. With adequate CPAP pressure the airway is acting essentially as a rigid tube, and flow is a function of effort: increasing effort produces increasing flow.

If the CPAP pressure is adequate to prevent apnoeas and snoring, but not adequate to achieve full patency, the airway now behaves like a floppy elastic tube, and increasing effort causes increasingly subatmospheric pressure, leading to progressive narrowing of the airway. Above a certain threshold effort, the airway narrows: the increased narrowing exactly compensates for the increasing effort, so flow becomes constant, independent of effort. Therefore the flow-vs-time curve will approximate a square wave as shown in the middle panel of FIG. 5.

In practice, if effort is only above the threshold flattening behavior during the middle part of the breath where effort is maximal, the flattening will be most noticeable over the middle half of the inspiration. Conversely, if effort is very high, inertial effects can lead to a brief period of high flow early in the breath, causing the initial overshoot shown in the right hand frame of FIG. 5. Hence, the present algorithm looks specifically at the middle half of the inspiration, not at the entire breath.

Figure 5:
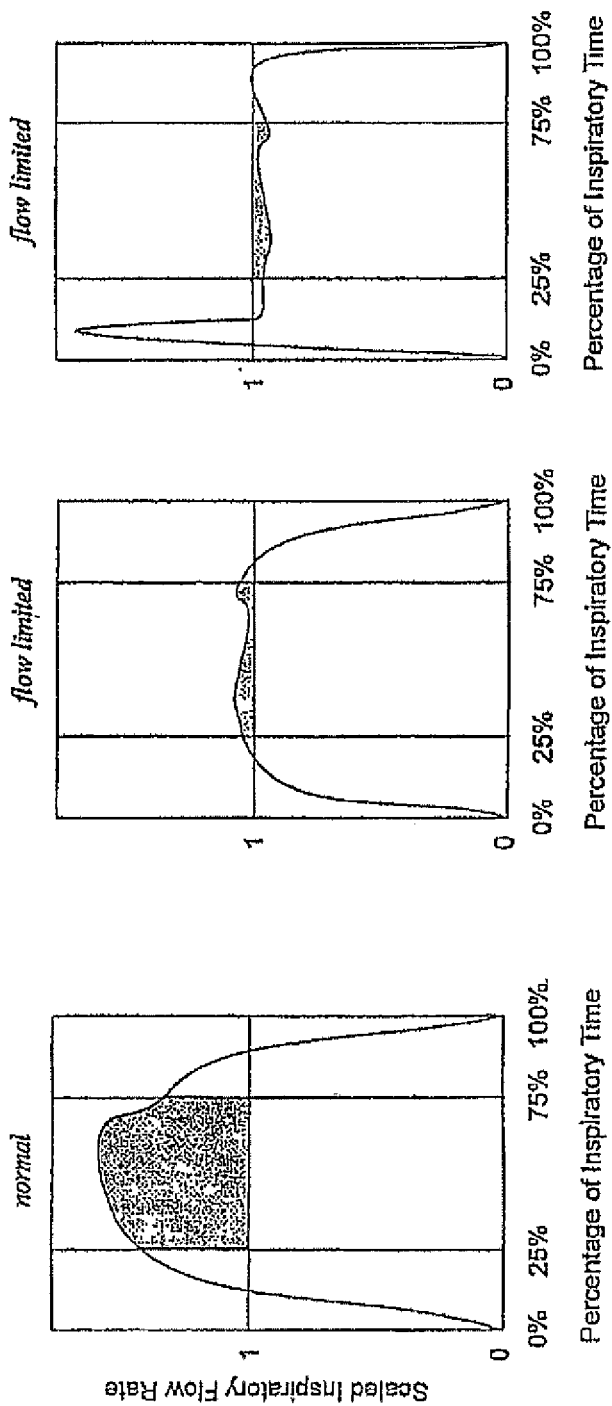
FIG. 5 shows normal and flow limited flow vs. time curves. The left hand panel shows a normal curve. The right hand panels show flow limited curves.

In FIG. 5, the inspiratory flow-vs.-time curve is scaled to unit duration and area. RMS deviation from unit flow is then calculated over the middle 50% of inspiratory time. The left hand panel shows a normal curve, where the RMS deviation is large, and the right hand panels show flow limited curves, with a small RMS deviation.

Figure 6:
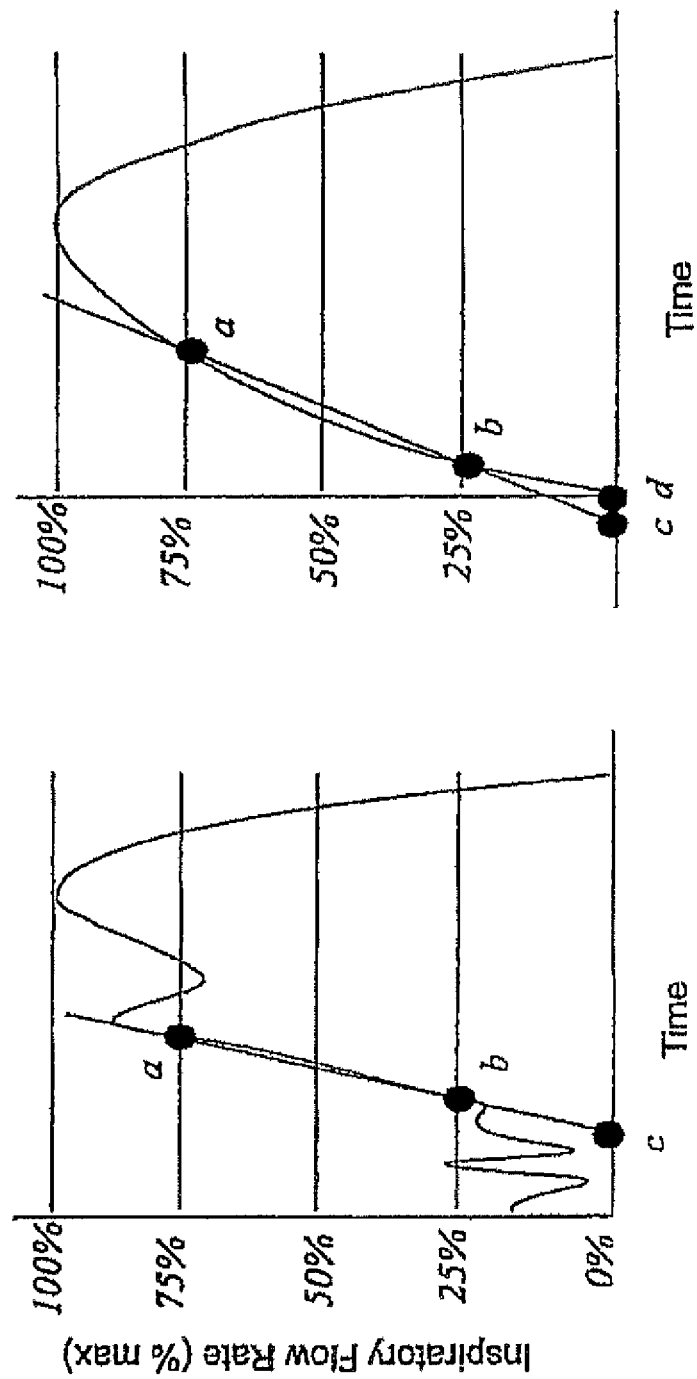
FIG. 6 shows inspiratory flow vs. time for two possible breaths.

A curvature or flattening index is derived, in order to quantify the degree of mid inspiratory flattening of the flow-time curve, using the following steps:

1. Referring to FIG. 6, any end-expiratory pause that has been included in the inspiratory half cycle is trimmed off as follows: Find where flow first reaches 75% of peak inspiratory flow "a", search backwards to the point where the flow last reached 25% of the peak "b", and extrapolate backwards to locate the time at which ray "ab" reaches the x-axis, i.e. to find the time where flow should be zero "c". This is taken as the earliest time at which inspiration could have started. In addition if "c" is to the left of origin "d", use origin "d".

2. The approximate effect of a 0.1 Hz low pass filter on the flow-time curve may be calculated and reversed as follows: (a) Pass the wave through an identical 0.1 Hz low pass filter a second time. (b) Subtract the doubly filtered wave from the singly filtered wave to give a first-order approximation of the effect of the filter. (c) Add this difference back to the original wave. Alternatively, this compensation for leak filter may be expected not to alter the results significantly and may therefore be removed for computation efficiency.

For breaths of interest, inspiratory duration is about seconds. The 0.1 Hz filter produces some distortion of the wave shape. For example, the trailing edge of a 2 second square wave sags by 20% of its amplitude, and the area under the curve is reduced by 10%. After correction, the trailing edge sags by only 2% of its amplitude, and the area under the curve is correct to 0.7%. The filter reduces the area under a sine wave by 10%, and after correction, the area is correct to 0.6%. This is more than adequate for our current purposes.

3. The effect of overshoot is normalized as will be described below.

4. The inspiratory flow-time curve is scaled to unit length and unit mean height. The scaling is because we are interested in the shape of the flow-time curve (rounded vs. flattened), not its amplitude or duration. Even with correct CPAP pressure, amplitude and duration are very variable, (particularly in REM sleep but also in stage 1 sleep and awake with sighs etc). Therefore, length and amplitude convey no important information about the adequacy of the CPAP pressure.

5. Breaths with grossly abnormal shapes are detected by comparing with a template.

Breaths that differ from the template by more than a threshold value at any point over the middle half are rejected. The default threshold is 1.0 unit.

6. The mean deviation of the inspiratory wave from the reference amplitude (M), for a middle portion of the wave is calculated. For example if the middle portion is one quarter of the inhalation wave and is centered then the mean deviation is:

$$MeanDeviation = \frac{\sum_{t=24}^{40}(fs(t)-M)}{16}$$

7. The Flattening Index (FI) is calculated as $$FI = \frac{MeanDeviation}{M}.$$

Typical values of the Flattening index for actual patients gives ~0.21 for normal curves; 0.15 is a threshold below which the device should increase the CPAP pressure.

8. If the breath is not rejected, a multiple breath pointwise moving average flow-time curve is updated, for example a 5 breath average.

The purpose of step 8 (averaging the waveform over 5 breaths) is to reduce the effect of cardiogenic airflow, which could disguise an otherwise flattened flow-time curve. Swallows, coughs, talking, etc can produce very abnormally shaped breaths. The purpose of step 5 is to prevent such breaths being included in the 5 breath average, which would delay the recognition of genuine flow limitation.

Step 8 may be unnecessary, because during flow limitation, cardiogenic pressure oscillations may not cause important changes in flow rate, due to effort independence. If this is the case, step 5 is also unnecessary, because coughs, swallows, etc will not be flat over the middle half of inspiration, and will therefore be correctly classified as not flow-limited.

Step 3, the normalization of overshoot, may be accomplished in several embodiments. This aspect of the invention assumes that 1) peak flow occurs close to middle portion of the wave, 2) the first $3^{rd}$ of the wave should have a generally positive gradient 3) the last third a generally negative gradient. 4) Any deviation from these conditions would indicate an overshoot.

In one embodiment the method comprises of 1) estimating peak flow in a middle portion of the wave, for example the middle third of the wave 2) any point outside that portion, for example in the first and/or last third of the said wave that exceeds the said peak flow is reset to the peak flow. This method therefore reduces the impact of the overshoot.

In a second embodiment the method comprises 1) estimating peak flow in the middle portion (e.g. a third) of the wave 2) any point outside that portion (e.g. in the first and/or last third of the said wave) that exceeds the peak flow is reset to the average of the sample before and after. 3) The process continues until no sample in the outside portions is greater than the peak flow. This method again reduces the impact of the overshoot—while also maintaining the shape of the waveform.

In a third (preferred) embodiment the method consists of 1) Dividing the wave into n parts and calculate mean amplitudes for each part. 2) Apply logic to determine what sort of wave the pattern indicates. 3) If overshoot is indicated, mark flattening as low.

In a fourth embodiment the method consists of 1) Calculating estimate of flattening for every n samples in the middle half of the wave (e.g. calculate flattening for sample 16 . . . 24, 17 . . . 25, and so on). 2) Marking the flattening index as the value that corresponds to the lowest value obtained for all sample permutations.

Alternative Statistical Calculation for M-Shape Detection

An alternative embodiment of the invention uses a different measure to determine whether an inspiratory wave pattern has an M shape. The technique is to decompose the inspiratory wave into a vector of features (floating point numbers) and a matrix pair of basis vectors that are orthogonal. Normalizing the time interval so that inspiration begins at zero and ends at B radians, the basis vectors may be chosen to be sin (Bt) and sin (3Bt). The inspiratory waveform is thus fit to the curve a sin (Bt)+b sin(3Bt), where a and b are determined by fitting the basis vectors to the inspiratory waveform in a least-squares sense using singular value decomposition. This is equivalent to finding the pseudo-inverse of the basis matrix and then multiplying the inspiratory waveform by this pseudo-inverse to find the factors. The pseudo-inverse can be calculated offline, i.e. not by the CPU contained in the ventilator.

To reduce the amount of calculation involved in this statistical calculation it is possible to map the [a,b] space for many patients and note the clusters into which the points representing the individual patients fall. The M-shaped breaths will be found clustered away from the non-M-shaped breaths. Thus whether a breath is M shaped can be determined by the Euclidean measure of distance from the M cluster center.

Example of M Shape Index Calculation

Figure 7:
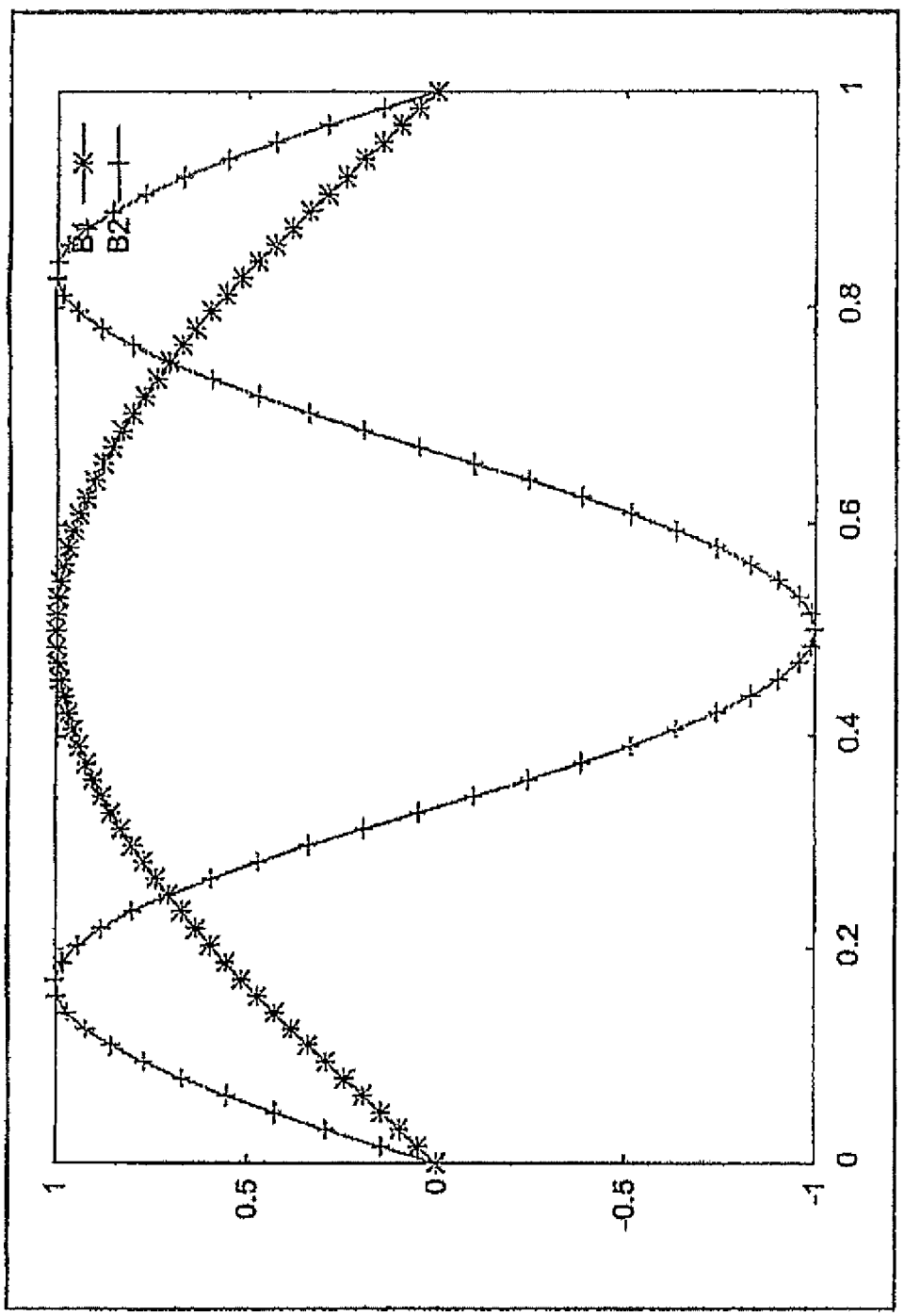
FIG. 7 is a graph of basis vectors for use in calculating an M shape index.

Each inspiration is interpolated over a grid of N points, preferably N=65. Two basis functions as shown in FIG. 7 are calculated for t=i/(N−1) where i goes from 0 to N−1, as $$B1 = \sin(\pi t)$$

$$B2 = \sin(3\pi t)$$

These basis functions can then be stored for use with all subsequent calculations of the M-shaped feature.

Each inspiration is then extracted and interpolated over a grid of N points. Two factors are then calculated as:

$$F_1 = \text{sum}(B1 \cdot fs)$$

where fs represents the interpolated inspiration points and • the dot-product operator.

The final shape value is obtained by normalising as:

$$\text{shape index} = \frac{F_2}{\sqrt{F_1^2 + F_2^2}}$$

This shape factor is then limited to vary between zero (purely sinusoidal) to one (very M-shaped).

Figure 8:
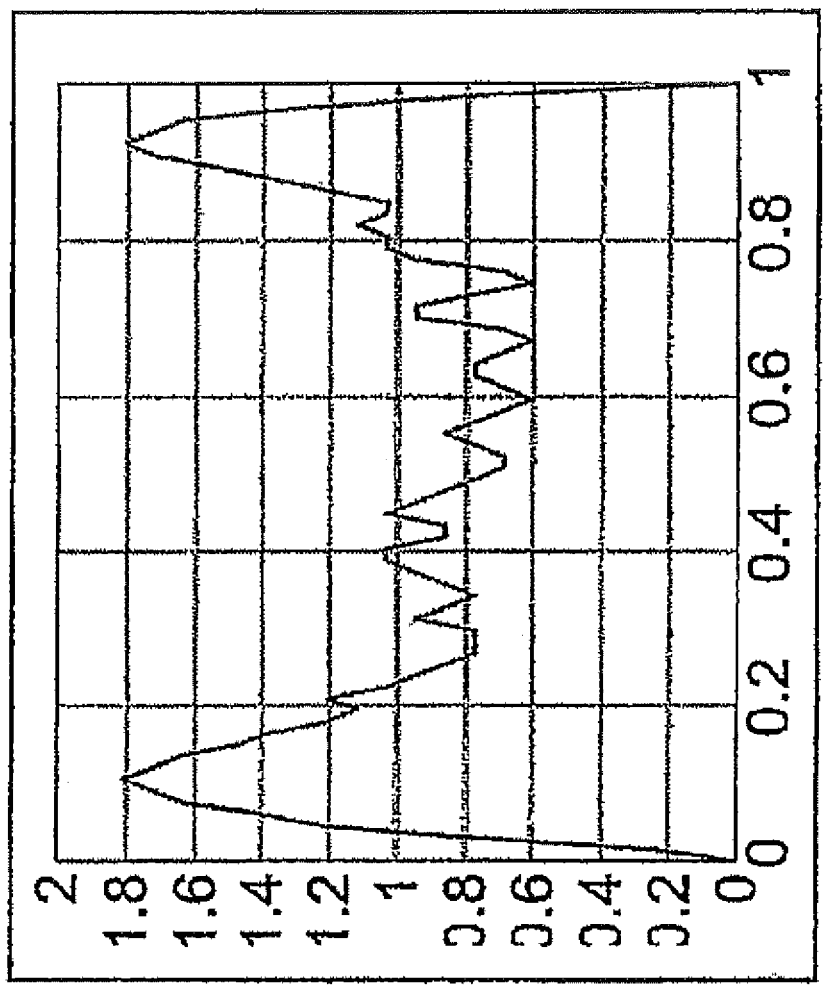
FIG. 8 is a graph of a typical M shaped breath.

For a typical M-shaped breath, as shown in FIG. 8, the above calculations yield $$F1 = 4.6082$$

$$F2 = 2.6538$$

and shape index=0.50. This may be contrasted with a typical non-flow limited breath that has an M-shape index of only about 0.2.

Although the invention has been described with reference to a particular embodiment, it is to be understood that this embodiment is merely illustrative of the application the principles of the invention. Thus, it is to be understood that numerous modifications may be made in the illustrative embodiment of the invention and other arrangements may be devised without departing from the spirit and scope of the invention. For example, while the preferred embodiment of the invention divides the waveform into specific segments for analysis and concentrates on the central values, other divisions and off center regions might equally apply.

The invention claimed is:

1. A respiratory apparatus, comprising:
   a flow detecting device to sense respiration and generate an inspiratory wave pattern; and
   a controller coupled to the flow detecting device, the controller configured to:
   decompose the inspiratory wave pattern into a matrix pair of basis vectors that are orthogonal;
   fit the basis vectors to the inspiratory wave pattern;
   determine factors associated with the basis vectors from the fitting; and
   determine a presence of a flow limited shape in the inspiratory wave pattern based on a function of the factors, the flow limited shape being indicative of an M-shaped breath.

2. The respiratory apparatus of claim 1, wherein each basis vector normalizes a time interval of the inspiratory wave pattern such that inspiration begins at zero and ends at a predetermined number of radians.

3. The respiratory apparatus of claim 2, wherein the basis vectors are sinusoidal functions of the predetermined number of radians.

4. The respiratory apparatus of claim 2, further comprising a motor operated blower, the motor operated blower coupled to the controller, wherein the controller is configured to adjust a setting for a treatment pressure generated with the motor operated blower in response to the determined presence of the flow limited shape.

5. The respiratory apparatus of claim 2 wherein the controller is configured to log an event based on the determined presence of the flow limited shape.

6. The respiratory apparatus of claim 1, wherein the basis vectors are sinusoidal.

7. The respiratory apparatus of claim 1, wherein the controller is configured to map the factors associated with the basis vectors to a first point in a space.

8. The respiratory apparatus of claim 7, wherein the space comprises a second point representing an M-shaped breath and a third point representing a non-M-shaped breath.

9. The respiratory apparatus of claim 8, wherein the controller is configured to calculate a measure of distance between the first point and the second point representing the M-shaped breath.

10. The respiratory apparatus of claim 1, wherein the controller is further configured to detect inspiration by:
    provisionally taking start of inspiration as a time that inspiratory airflow exceeds a predetermined threshold,
    rejecting the start of inspiration if the airflow then falls below zero again before a total volume reaches a predetermined value,
    provisionally taking end of inspiration as a time that the airflow falls below zero after the total volume reaches a predetermined value, and
    rejecting the end of inspiration if the airflow then goes above a second predetermined value in an inspiratory direction before the total volume expired reaches a third predetermined value.

11. A respiratory apparatus, comprising:
    a flow detecting device to sense breath; and
    a controller coupled to the flow detecting device, the controller configured to:
    interpolate an inspiratory portion of the breath;
    calculate a first factor as a function of a first basis function and the interpolated inspiratory portion of the breath;

calculate a second factor as a function of a second basis function and the interpolated inspiratory portion of the breath; and determine whether the breath is flow limited based on the first and second factors, wherein the flow limited breath is indicative of an M-shaped breath.

12. The respiratory apparatus as claimed in claim 11, wherein the basis functions are sinusoidal.

13. The respiratory apparatus of claim 11, wherein the first basis function is sin(itt), and the second basis function is sin(3πt).

14. The respiratory apparatus of claim 11, wherein the controller is configured to store the basis functions for use with a subsequent calculation.

15. The respiratory apparatus of claim 11, wherein the controller is configured to derive a shape index based on the first and second factors.

16. The respiratory apparatus as claimed in claim 15, wherein the shape index is computed by a formula:

$$\text{shape index} = \frac{F_2}{\sqrt{F_1^2 + F_2^2}},$$

wherein $F_1$ and $F_2$ represent the first factor and the second factor, respectively.

17. The respiratory apparatus of claim 15, wherein the controller is configured to determine whether the breath is flow limited by comparing the shape index to a threshold indicative of a non-flow-limited breath.

18. The respiratory apparatus of claim 11, wherein the controller is further configured to detect inspiration by:

provisionally taking start of inspiration as a time that inspiratory airflow exceeds a predetermined threshold, rejecting the start of inspiration if the airflow then falls below zero again before a total volume reaches a predetermined value, provisionally taking end of inspiration as a time that the airflow falls below zero after the total volume reaches a predetermined value, and rejecting the end of inspiration if the airflow then goes above a second predetermined value in an inspiratory direction before the total volume expired reaches a third predetermined value.

19. The respiratory apparatus of claim 11, further comprising a motor operated blower, the motor operated blower coupled to the controller, wherein the controller is configured to adjust a setting for a treatment pressure generated with the motor operated blower in response to the determined flow limited breath.

20. The respiratory apparatus of claim 11 wherein the controller is configured to log an event based on the determined flow limited breath.

21. A method for determining whether an inspiratory wave pattern has an M-shape, comprising:

sensing respiration and generating an inspiratory wave pattern;

decomposing the inspiratory wave pattern into a matrix pair of basis vectors that are orthogonal;

fitting the basis vectors to the inspiratory wave pattern;

determining factors associated with the basis vectors from the fitting; and determining a presence of a flow limited shape in the inspiratory wave pattern based on a function of the factors, the flow limited shape being indicative of an M-shaped breath.

22. A method for determining whether an inspiratory wave pattern has an M-shape, comprising:

sensing breath;

interpolating an inspiratory portion of the breath;

calculating a first factor as a function of a first basis function and the interpolated inspiratory portion of the breath;

calculating a second factor as a function of a second basis function and the interpolated inspiratory portion of the breath; and determining whether the breath is flow limited based on the first and second factors, wherein the flow limited breath is indicative of an M-shaped breath.

* * * * *